United States Patent
Marshall

(10) Patent No.: US 7,179,455 B2
(45) Date of Patent: Feb. 20, 2007

(54) PESTICIDE IN GEL FORM

(75) Inventor: Robert John Marshall, Christchurch (NZ)

(73) Assignee: Kiwicare Corporation Limited, Christchurch (NZ)

( * ) Notice: Subject to any disclaimer, the term of this patent is extended or adjusted under 35 U.S.C. 154(b) by 225 days.

(21) Appl. No.: 10/435,668

(22) Filed: May 12, 2003

(65) Prior Publication Data

US 2004/0180071 A1 Sep. 16, 2004

Related U.S. Application Data

(63) Continuation of application No. 09/743,197, filed as application No. PCT/NZ99/00104 on Jul. 2, 1999, now abandoned.

(30) Foreign Application Priority Data

Jul. 8, 1998 (NZ) .................................. 330949

(51) Int. Cl.
*A01N 65/00* (2006.01)
(52) U.S. Cl. .................. 424/84; 424/405; 424/406; 514/546; 514/343; 514/27; 514/26; 514/167; 514/613; 514/920
(58) Field of Classification Search ............ 424/84, 424/405, 406
See application file for complete search history.

(56) References Cited

U.S. PATENT DOCUMENTS 4,520,015 A 5/1985 Pesche ...................... 424/153

2004/0028713 A1 * 2/2004 Hesse et al. ................ 424/405

FOREIGN PATENT DOCUMENTS

| GB | 1371135 | * | 7/1975 |
| GB | 2305607 | A | 4/1997 |
| WO | 85/00752 | * | 2/1985 |
| WO | WO85/04074 | | 9/1985 |
| WO | WO91/07972 | | 6/1991 |

OTHER PUBLICATIONS

Bitrex McFarland-Smith Sep. 1988.*
Derwent Abstract Accession No. 88-357032/50, JP 63267361 A (SAN EI CHEM IND KK), Nov. 4, 1988.
Derwent Abstract Accession No. 93-382967/48, JP 05286810 A (Aritsune Yakuhin Kogyo KK), Nov. 2, 1993.
Derwent Abstract Accession No. 97-444036/41, JP 09202701 A (Earth Seiyaku KK), Aug. 5, 1997.
Derwent Abstract Accession No. 97/487892/45, RU 2077200 C (RET RES Commercial Firm), Apr. 20, 1997.
Derwent Abstract Accession No. 98-592657/50, RU 2110916 C (Fedotov A S), May 20, 1998.
The Pesticide Manual, Tenth Edition, pub. 1994 by the British Crop Protection Council, pp. 116, 735, 918, 1043 and 1120.
The Merck Index, Eleventh Edition, pub. 1989 by Merck & Co., Rahway, p. 117, entry No. 113.

* cited by examiner

*Primary Examiner*—Neil S. Levy
(74) *Attorney, Agent, or Firm*—Jacobson Holman PLLC

(57) ABSTRACT

The invention relates to a bait matrix which includes a gelling agent and a pesticide. The bait matrix is useful for controlling pests by attracting and poisoning them. The gel matrix is substantially weatherproof and hence can be used when exposed to the weather.

9 Claims, No Drawings

PESTICIDE IN GEL FORM

This is a Continuation of application Ser. No. 09/743,197 filed Mar. 8, 2001; which in turn is a Nationalization of PCT/NZ99/00104 filed Jul. 2, 1999.

FIELD OF INVENTION

The invention relates to a newly developed gel. The gel may be used as the matrix or basis for a bait product for controlling pests. However, other uses are envisaged.

BACKGROUND OF THE INVENTION

Animal baits are limited to cereal pellet, carrot, and paste. None of these are durable and those that are available to farmers are either expensive or relatively ineffective Known pest control compositions which use vertebrate pesticides are vulnerable due to the high annual cost and also due to the increasing scrutiny being placed on pesticide usage worldwide. Market access for agriculture produce could be threatened if food production methods fail to meet the increasingly stringent standards demanded by consumers. Careful management is required to provide confidence and safety of the pesticide. This must be based on toxicological data relating to public health and environmental effects and strategies for minimising risks.

One possible environmental effect is the risk of poisoning of non target species. Examples of accidental poisoning have been demonstrated for native birds, native bats, invertebrates including honeybees, deer, livestock and domestic pets. Deaths are always undesirable even for common species and unacceptable for rarer species, populations of which may be unable to withstand such losses.

There is a requirement for a bait product which is weatherproof and therefore durable when placed out in the open weather. A bait product which could be handled easily and which does not disintegrate in the user's hands would also be an advantage.

SUMMARY OF THE INVENTION

It is an object of the invention to go some way in overcoming the disadvantages with known bait product systems or to at least provide the public with a useful choice.

It is also an object of the present invention to provide a novel gel which is substantially weatherproof or to at least provide the public with a useful choice.

The invention provides a substantially weatherproof gel. The invention also provides a gelling system which is substantially resistant to dehydration.

The invention also provides a gelling system which includes an active ingredient and which provides for the slow release of the active ingredient.

The invention also provides a pesticide composition comprising a gelling agent and a pesticide and optionally other ingredients.

Gelling agents such as carrageenan or sodium alginate may be used. Two gelling agents may be used together.

The pesticide 1080 (sodium fluoroacetate) may be incorporated in the gel. However other pesticides are envisaged such as cholecalciferol (Vitamin $D_3$). Other toxins could be used such as nicotine, aconitine or scilliroside or $\alpha$-chloralose. Sodium fluoroacetate may be used in an amount of 1.5 g/kg. Cholecalciferol may be used in an amount of 6 g/kg.

Optional Ingredients Include:

an attractant to attract the pest and/or mask the taste of the pesticide. An orange flavour may be added for example to gels used to kill possums. A Preservative may be added. This may, for example be Glydant Plus. However other preservatives may be used such as Delvocid, Suttocide A, sodium metabisulphite and potassium sorbate.

Bitrex is also an optional ingredient. This is a human deterrent. Other deterrents which could be used include cinnamamide/diatite bird repellent. Dye may be added.

The gel preferably has a relatively low dehydration rate such that it is adapted to subsist in the open environment for at least a month.

The gel is preferably adapted to target the pest of interest but adapted such that it does not attract and will non-target other animals.

Embodiments of the invention will now be described, by way of example only.

DETAILED DESCRIPTION OF THE INVENTION

Example 1

The following example details the ingredients in a gel composition containing the pesticide 1080 (sodium fluoroacetate). Such a pesticide would be useful, for example to kill possums. Table 1 describes the ingredients in the composition.

The carrageenan and sodium alginate are gelling agents. The orange flavour is an attractant and masks the taste of the 1080. The Glydan Plus is a preservative and bitrex is a very bitter substance. Bitrex is included as a safety control to deter humans and in particular children from eating the gel based poison. It will be readily appreciated that the 1080 can be substituted by any other poisons such as cholecalciferol (Vitamin D3).

Preservatives and stabilisers are included to ensure that the composition has a shelf life of at least one year.

The composition may be supplied ready for use in a purpose designed bait station.

Table 2 details the physical/chemical properties of the composition.

In field use, the bait is very resistant to dehydration losing a maximum of 14% weight when left in exposed situations for three months. The gel is also resistant to direct rainfall before noticeable loss of shape occurs and drainage holes ensure that water does not collect in the bait station. The durability of the bait in the field means that it can be used sparingly (and hence economically), and at a recommended dispersion of no more than one to two bait stations per hectare.

Example 2

The bait station

The bait station is made from 2–3 mm thick plastic to withstand animals chewing. It is designed so that the targeted animals can easily access the bait through the front opening.

To assess the likely exposure of non-target species to a hazardous material, a pen trial was conducted to measure the amount of spillage that occurs when opossums feed at gel bait stations.

Example 3

Spillage of Bait from Bait Stations

Four possums maintained in an outdoor pen measuring 5×5 m were each presented with a gel bait station containing 300 g gel, and a 'Killmore' bait station (as commonly used in possum control) containing 300 g RS5 pellet baits. The bait stations were fitted to vertical fence posts such that the lowest part of the opening of each bait station was 35 cm above ground. This is a convenient height for possums to feed from bait stations while standing on the ground. Bait stations were reweighed after each 24 hour period for eight days and the amount of each bait type eaten calculated. Baits and bait fragments that were spilled during each 24 hour period were collected and weighed.

During the eight nights for which possums fed on baits, only 0.1 g on average was split each night, compared with 3.3 g of pellets (Table 3). Expressed as a percentage of the amounts eaten, the overall mean weight of gel split was 0.3%, which was significantly less than the 3.2% of RS5 pellets split.

TABLE 1

FORMULATED PRODUCT

Composition (if necessary continue onto a separate sheet)

| Common Name/Trade name (use common names where possible) | Chemical Name where: a A trade name is given b There is no common name | Purpose (eg active ingredient, wetter, surfactant) | Concentration either in g/litre(liquids) or g/kg (solids) |
|---|---|---|---|
| WATER | | VEHICLE | 285.78 |
| TSP | | pH ADJUSTMENT | 2.0 |
| SUGAR | | GEL CONTROL & PALATABILITY | 490.0 |
| GLUOCSE SYRUP | | EVAPORATION CONTROL | 180.0 |
| DYE | | 1080 COLOUR IDENTIFICATION CODE | 1.00 |
| CARRAGEENAN | | THICKENER | 15.0 |
| SODIUM ALGINATE | | THICKENER | 14.0 |
| ORANGE FLAVOUR | | 1080 MASK AND PALATABILITY | 10.0 |
| SODIUM HYDROXIDE | | pH ADJUSTER | QS TO 9.0 |
| SODIUM FLUOROACETATE | | ACTIVE | 1.5 |
| GLYDANT PLUS | DMDM EYDANTOIN + 3-IODO-2-PROPYNYL CARBAMATE | PRESERVATIVE | 0.7 |
| BITREX | DENATONIUM BENZOATE | SAFETY CONTROL | 0.02 |

TABLE 2

PHYSICAL/CHEMICAL PROPERTIES OF PRODUCT

| | |
|---|---|
| Storage Stability | GOOD |
| Density (Liquids only) | N/A |
| Flammability (liquids - cashpoint, solids - whether flammable or not | N/A |
| Acidity (where relevant) | — |
| Alkalinity (where relevant) | pH 9.0 |
| Colour | GREEN |
| Particle size range (where relevant) | N/A |
| Chemicals with which product is known to be: | |
| (a) Compatible | N/A |
| (b) Incompatible | N/A |
| Other properties eg corrosiveness | NOT CORROSIVE |
| Stability (in hours) of stated field dilutions | N/A |

TABLE 3

Spillage of RS5 pellets and gel bait expressed as daily mean per possum, and as a percentage of the mean weight of each bait type eaten each day.

| | RS5 pellet | | Gel bait | |
|---|---|---|---|---|
| Day | Mean weight spilled (g) per possum | Mean spillage as a % of mean weight of bait eaten | Mean weight spilled (g) per possum | Mean spillage as a % of mean weight of bait eaten |
| 1 | 3.8 | 2.6 | 0.1 | 0.1 |
| 2 | 3.1 | 1.0 | 0 | 0 |
| 3 | 4.0 | 9.0 | 0 | 0 |
| 4 | 4.5 | 8.0 | 0.5 | 0.9 |
| 5 | 3.8 | 7.8 | 0.3 | 0.5 |
| 6 | 3.0 | 4.3 | 0 | 0 |
| 7 | 1.1 | 3.8 | 0 | 0 |
| 8 | 2.9 | 6.8 | 0 | 0 |

Example 4

Palatability of Gel Bait to Non-Target Species

The responses of a range of non target animals to gel bait were observed to assess palatability of the bait. Apple paste bait was also presented to these animals as a control treatment. This bait type has been used for many years as possum bait.

a) Native Birds

The responses of groups of captive fruit-eating birds to gel bait were observed at Orana Park, Christchurch. Species, which were observed as groups of individuals, were kaka (n=3), brown kiwi (2), kea (6), kereru (4), and kakariki (5). Gel bait (100 g) was presented in plastic dishes to each bird species on two days for eight hours. On separate days the birds were also presented with two varieties of apple paste bait, BB13 and BB3 (Animal Control Products Ltd. Wanganui). The daily order of presentation of pastes to birds was randomised and birds' normal diet was maintained throughout trials, The response to baits of two individual birds of each species was observed during the first 30 minutes for which baits were presented each day.

The responses of native birds (listed in Table 4) in the wild to gel baits were observed at a site on the edge of mixed beech (Nothofagus sp) forest at Bullock Creek, Paparoa National Park. Gel bait and two types of apple paste bait, BB13 and BB16 (Animal Control Products Ltd, Wanganui) were placed in separate bowls (100 g per bowl) on four tree-mounted platforms with fuschia flowers as an attractant, and in four bowls sited on the ground. They were observed for two hours from dawn and two hours before dusk each day for seven days. The same baits were used throughout the study to simulate normal field presentation, but they were removed at night to prevent possums from eating them.

In both the pen and field studies, the main data recorded were the time spent feeding on each bait type and the amount eaten. Control samples, unavailable to birds, were used to provide correction for weight variation due to climate.

b) Honey Bees

Approximately 200 forager bees were trained to feed on sugar (sucrose) syrup at a table placed 20 m away from a hive. Gel bait, and 'BB13' apple paste bait known to be attractive to bees (Goodwin & Ten Houten 1991), were presented to the bees by placing 2 g of each material separately in Petri dishes. Ten dishes of each bait type were placed randomly on the table with 10 cm separating dishes. The number of bees visiting the two bait types was compared by counting the number of bees at each type during 10 minute sampling periods. Twelve sampling periods were used, distributed between 10–15 hours during fine weather.

c) Invertebrates and Skinks

Time-lapse video recording was used to monitor the response of common skinks, large headed weta, common snails, and ground beetles to gel bait and BB13 apple paste. Between six and 10 individuals of each species were housed together in glass tanks (0.72×0.38×0.38 m). Tanks for weta, snails and beetles had a floor-lining of soil, leaf-litter and sphagnum moss. Small logs with a hollow core were provided for shelter for weta, as recommended by Barrett (1991). Snails and beetles sought shelter in the leaf litter. Tanks for skinks had a floor-lining of fine shingle and stones and bark were provided as shelter. Fresh native plant material and apple was supplied every two days, and processed pet meat was supplied every two weeks. Water was always freely available for all animals.

Approximately 10 g gel bait was placed on plastic beaker lids and activity was monitored for two overnight periods of 16 hours for each group of animals. For each species, the total number of encounters with bait (ie. contact with bait), the number of feeding sessions, and the total time spent feeding were recorded.

d) Short-Tailed Bats

Gel baits and BB13 apple paste baits weighing 100 g were presented to six uniquely marked short-tailed bats, maintained on behalf of the Department of Conservation at Wellington Zoo. Baits were presented in Petri dishes for the first three hours of each night during the normal main feeding period. Honey-water (ie. an aqueous solution of X % honey), which was part of the bats' normal diet, was presented on two nights as a positive control. Time spent feeding on baits or honey water was monitored using video equipment and infra-red illumination. The weight of bait or honey eaten was calculated at the end of the three hour observation period.

Results a) Native Birds

Of the six species observed at Orana Park, four ate appreciable quantities of apple paste, while kereru and kakariki ate only small amounts (Table 4). By contrast, kea was the only species to cat significant amounts of gel bait. A total of 87 g was eaten by the six birds over two days. Three weka ate a total of about 1 g of bait.

Table 4

Mean weight (g) of gel and two types of apple paste eaten per bird. Six native species of captive birds were presented with bait during two days.

TABLE 4

Mean weight (g) of gel and two types of apple paste eaten per bird. Six native species of captive birds were presented with bait during two days.

| Common name (see Appendix 1 for generic names) | BB13 paste | BB16 paste | Gel bait |
|---|---|---|---|
| Kaka | 8.6 | 2.0 | 0.0 |
| Brown kiwi | 7.0 | 17.9 | 0.1 |
| Weka | 19.6 | 0.3 | 0.4 |
| Kea | 5.1 | 2.8 | 14.4 |
| Kereru | 0.5 | 1.0 | 0.0 |
| Kakariki | 1.3 | 0.0 | 0.0 |
| All species | 42.2 | 24.0 | 14.9 |

Of the 16 species observed in the field study area, four were observed approaching within 3 m of a bait bowl, altogether on 17 occasions (Table 5) However, none of these species, which included two flocks of silvereye, actually encountered or fed on bait. Only two of the sixteen species, weka (a family of three individuals) and robin (three individuals), were actually observed interacting with baits. Weka interacted only with the baits that were presented on the ground while robin interacted with the baits on the platforms as well as those placed at ground level. Approximately 98% of the total time spent feeding on gel by birds was attributable to weka, which fed approximately equally an paste bait (47%) and gel bait (51%). The small amount of feeding by robin was mainly on paste (1.5%) rather than gel (0.5%).

Table 5

The number of times bird of 6 species were seen near and encountering baits, and the total time spent feeding on bait by each species. Eleven other species present at the study site were not seen closer than 3 m from the gel bait.

TABLE 5

The number of times bird of 6 species were seen near and encountering baits, and the total time spent feeding on bait by each species. Eleven other species (see Appendix 1) present at the study site were not seen closer than 3 m from the gel bait.

| Common Name (see Appendix 1 for generic name) | No. of occasions seen within 3 m, but without encountering bait | No. bait encounters | | Total time spent investigating or feeding on bait (min) | |
|---|---|---|---|---|---|
| | | BB13 | Gel | BB13 | Gel |
| Bellbird | 6 | 0 | 0 | 0 | 0 |
| Fantail | 1 | 0 | 0 | 0 | 0 |
| Silvereye | 2 (flocks) | 0 | 0 | 0 | 0 |
| South Island robin | 0 | 2 | 1 | 0.5 | 0.2 |
| Tui | 6 | 0 | 0 | 0 | 0 |
| Weka | 0 | 19 | 27 | 14.7 | 16.9 | b) Honey Bees

The total number of bees present during all counts combined for each bait type (ie. 120 10 minute counts) was 154 for BB13 paste and 12 for gel bait. The mean number of bees observed on dishes for each 10 minute sample period was significantly less for gel bait (mean=0.1) than for BB13 paste (mean=1.28) (paired 't'=13.4, d.f.=10, p<0.001). Bees appeared to be feeding on the paste bait throughout most of the time spent on this bait type as the proboscis of most bees could be clearly seen penetrating the surface of the bait. However, due to the firmer texture of the gel, bees were not able to penetrate the surface and it is likely that most of the time was spent investigating the bait and attempting, unsuccessfully, to feed on it.

c) Invertebrates and Skinks

Some of the small non-target animals observed in laboratory tanks were seen feeding on baits. Snails (three out of eight observed) and weta (one of eight) fed on gel bait, while snails (one of eight), weta (two of eight), and skinks (two of 10) fed on BB13 paste (Table 6).

Table 6

Feeding responses of skinks, weta, snails and ground beetles to gel and paste bait. Baits were presented to each group of animals for two overnight periods of 16 hours.

TABLE 6

Feeding response of skinks, weta, snails, and ground beetles to gel and paste bait. Baits were presented to each group of animals for 2 overnight periods of 16 h.

| Common name (see Appendix 1 for generic name) | No. animals in group | Gel | | | BB13 paste | | |
|---|---|---|---|---|---|---|---|
| | | No. investigations | No. feedings | Total feeding time (min) | No. investigations | No. feedings | Total feeding time (min) |
| Skinks | 8 | 2 | 0 | 0 | 8 | 2 | 2.8 |
| Weta | 10 | 5 | 1 | 0.3 | 2 | 2 | 5.9 |
| Snails | 8 | 3 | 3 | 39.4 | 1 | 1 | 21.5 |
| Beetles | 6 | 0 | 0 | 0 | 4 | 0 | 0 | d) Short-Tailed Bats

Short-tailed bats were observed visiting all food types. However, while they fed vigorously on honey water and BB13 apple paste, they did not feed on gel bait (Table 7).

Table 7

Feeding response of six short-tailed bats presented with gel and paste baits and honey water for three hours on different nights. Results for all bats are combined.

TABLE 7

Feeding response of six short-tailed bars presented with gel and paste baits and honey water for 3 h on different nights. Results for all bars are combined.

| Food type | Number of visits | % of visits where feeding definitely occurred | % of visits where feeding possibly occurred | Weight of bait eaten (g) |
|---|---|---|---|---|
| Honey water | 23 | 78 | 4 | 4.24 |
| Honey water | 51 | 65 | 14 | 8.01 |
| BB13 paste | 68 | 88 | 1.5 | 5.73 |
| Gel bait | 52 | 0 | 0 | 0.0 |

Where specific processing steps, materials and apparatus have been described, and known equivalents exist, such equivalents are incorporated as if specifically set forth.

It is to be understood that the scope of the invention is not limited to the described embodiments and therefore that numerous variations and modifications may be made to these embodiments without departing from the scope of the invention as set out in the specification.

Although a gel has been described incorporating the poison 1080 which has specifically been trialled for possums, it is envisaged that poison in an amount and of a type suitable for ferrets, stouts, weasels, deer, pigs, tar and chamois could be used. Poisons suitable for coyotes, groundhogs, rodents of all kinds and snakes could also be used in such a gelling system.

Poison in the above described gelling system may also be used to control undesirable birds such as for example, crows, rooks, pigeons and the like.

It will be appreciated that whilst certain animals are undesirable in any particular region, they may be desirable in others.

Poison may be used in the above gel composition to kill wasps.

The gelling composition may be used above or below ground. It may be placed using aerial placement or ground placement.

The gelling system may be used as a waterproof feeding system for aquaculture such as salmon farming, prawns, shrimp and crayfish farming.

It may also be used as a medium for processed imitation meats or processed foods for vegans and/or vegetarians.

Industrial Applicability

The gel matrix is useful for attracting and poisoning pests. It may be used outside as it is substantially resistant to weather elements. It is able to be handled easily and does not disintegrate in a user's hands or when exposed to the elements. Pests are an environment nuisance and their targeted removal is of environmental benefit.

The invention claimed is:

1. A pesticide bait matrix which maintains its function and efficacy as a pesticide bait matrix under adverse weather conditions in an open environment for at least one month, the matrix comprising a gelling system which is resistant to dehydration, the gelling system comprising:

at least one gelling agent that is resistant to adverse weather conditions, wherein the gelling agent includes carrageenan or sodium alginate;

a preservative that is a member selected from the group consisting of DMDM hydantoin with iodopropynyl butylcarbamate; natamycin; sodium hydroxymethylglycinate; sodium metabisulphite and potassium sorbate;

glucose syrup to control evaporation;

an attractant;

a non-target species deterrent; and a pesticide that is a member selected from the group consisting of sodium fluoroacetate, cholecalciferol, nicotine, aconitine, scilliroside and α-chloralose;

wherein the pesticide bait matrix has a field life of at least one year, and a resistance to dehydration such that it loses at most 14 percent weight on exposure to the open environment for three months.

2. The bait matrix according to claim 1 in which the gelling agent is carrageenan.

3. The bait matrix according to claim 1 which comprises two gelling agents.

4. The bait matrix according to claim 1 in which the attractant has an orange, apple or honey flavour which attracts pest or masks the tastes of the pesticide.

5. The bait matrix according to claim 1 in which the non-target species deterrent is denatonium benzoate for deterring human or cinnamide for deterring birds.

6. The bait matrix according to claim 1 which further comprises a dye.

7. The bait matrix according to claim 1 wherein the pesticide is a pesticide for controlling vertebrate pest.

8. A pesticide bait matrix which maintains its function and efficacy as a pesticide bait matrix under adverse weather conditions in an open environment for at least one month, the matrix comprising a gelling system which is resistant to dehydration, the gelling system comprising:

at least one gelling agent that is resistant to adverse weather conditions, wherein the gelling agent includes carrageenan;

a preservative that is a member selected from the group consisting of DMDM hydantoin with iodopropynyl butylcarbamate; natamycin; sodium hydroxymethylglycinate; sodium metabisulphite and potassium sorbate;

glucose syrup to control evaporation;

an attractant;

denatonium benzoate or cinnamamide; and a pesticide that is a member selected from the group consisting of sodium fluoroacetate, cholecalciferol, nicotine, aconitine, scilliroside and α-chloralose;

wherein the pesticide bait matrix has a field life of at least one year, and a resistance to dehydration such that it loses at most 14 percent weight on exposure to the open environment for three months.

9. The bait matrix according to claim 8 in which the attractant has an orange, apple or honey flavour which attracts pest or masks the tastes of the pesticide.

* * * * *